United States Patent [19]

Mankin

[11] Patent Number: 5,958,695
[45] Date of Patent: Sep. 28, 1999

[54] METHOD OF SCREENING TO FIND NEW ANTIBIOTICS

[75] Inventor: Alexander Mankin, Oak Park, Ill.

[73] Assignee: The Board of Trustees of the University of Illinois, Ill.

[21] Appl. No.: 09/007,897

[22] Filed: Jan. 15, 1998

[51] Int. Cl.[6] ...................................................... C12Q 1/68
[52] U.S. Cl. ............................................................. 435/6
[58] Field of Search .................................................. 435/6

[56] References Cited

PUBLICATIONS

Gu et al., *PNAS*, vol. 91, 1994, pp. 5612–5616, Jun. 1994.

*Primary Examiner*—James Ketter
*Attorney, Agent, or Firm*—Bierman, Muserlian and Lucas

[57] ABSTRACT

An easily automated method of screening for antibiotics active against erythromycin resistant strains, comprising footprinting an antibiotic on the domain II of 23S rRNA, isolating rRNA by incubating an antibiotic with ribosomes, modifying ribosomes with a chemical modifying agent, isolating modified rRNA and subjecting it to the reverse transcriptase-mediated primer extension and gel electrophoresis on a DNA sequencer to determine the extent of antibiotic-induced protection of an rRNA nucleotide from chemical modification.

8 Claims, 1 Drawing Sheet

METHOD OF SCREENING TO FIND NEW ANTIBIOTICS

OBJECTS OF THE INVENTION

It is an object of the invention to provide a method of screening compounds to ascertain their potential as antibiotics in an automated manner.

This and other objects and advantages of the invention will become obvious from the following detailed description.

THE INVENTION

The novel method of screening for the antibiotics active against erythromycin-resistant strains comprises footprinting an antibiotic on domain II of 23S rRNA by incubating an antibiotic with ribosomes, modifying ribosomes with a chemical modifying agent, isolating modified rRNA and subjecting it to the reverse transcriptase-mediated primer extension and gel electrophoresis on a DNA sequencer to determine the extent of antibiotic-induced protection of an rRNA nucleotide from chemical modification.

Preferably, all three steps of the method are performed in a 96 well plate format and the extension products are analyzed in an automated DNA sequencer. This makes it possible to screen a large number of compounds at the same time in an automated fashion. Ribosomes from *Escherichia coli* or any other suitable source in an appropriate buffer are placed in the wells and incubated with an antibiotic at an appropriate temperature for a period of time to permit antibiotic binding to the ribosome. Then, dimethyl sulfate (DMS) or another RNA modifying agent is added to the wells and a brief incubation takes place during which ribosomal RNA is modified at specific residues. Excess of modifying agent is quenched by addition of an appropriate chemical reagent (such as mercaptoethanol when using DMS).

Then, RNA is isolated simultaneously from all the modified samples using commercially available 96-well format purification kits such as RNeasy 96™ from Qiagen, where the addition of a chaotropic salt such as guanidium thiocyanate leads to the dissociation of ribosomal proteins from rRNA with selective binding of the released rRNA to the resin followed by elution thereof with water.

As a result of the RNA isolation, modified rRNA is collected as an aqueous solution in another 96 well plate. The primer extension is performed preferably with a fluorescent dye labelled oligodeoxy ribonucleotide primer complementary to rRNA downstream from the analyzed portion which is mixed with the rRNA in the wells of the plate. After annealing of the primer to rRNA, a mixture of three deoxy nucleoside triphosphates and one dideoxy nucleoside triphosphate terminator is added and the primer is extended to the first nucleoside complementary to the terminator. The main extension product has a defined length in contrast to the regular footprinting in which a ladder of bands is generated. During extension of the primer to the first terminator, reverse transcriptase will pause at the DMS-modified A752.

The reaction products from each well of a 96 well plate are directly loaded onto a slot of a sequencing gel which will be run on an automated DNA sequencer. There will be few main bands in each sample, including a band corresponding to the primer itself, a band corresponding to the reverse transcriptase pausing at the methylated A752 and a band corresponding to the primer extended to the first incorporated terminator. A DNA sequencer scans the gel slots and quantifies the intensity of the fluorescent band. The ratio between the longest band, the terminator band and the band corresponding to the pause at A752 shows the extent of A752 protection by the tested antibiotic.

Since only several bands in a very narrow size range are expected to be present on the sequencing gel, several different samples can be loaded onto the same slot of a gel after specific time intervals. Therefore, one gel can be used to analyze more than a hundred samples.

Referring now to the drawings.

Figure 1:
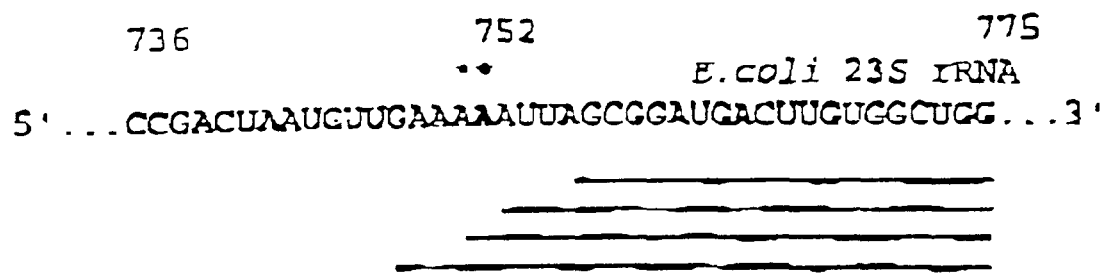
FIG. 1 is a segment of *E. coli* 23S rRNA corresponding to positions 736 to 775 (SEQ ID NO:1) wherein positions accessible for DMS modification are indicated by asterisks (*).
Figure 2:
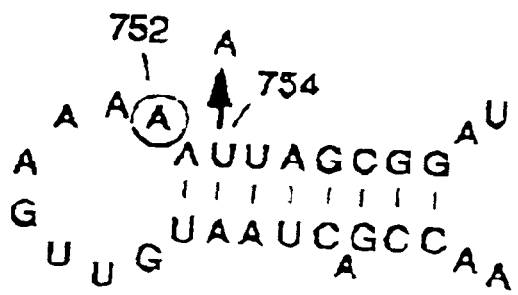
FIG. 2 is a segment of *E. coli* 23S rRNA corresponding to hairpin positions 736 to 760 with the position protected by ketolides from chemical modification is circled and a mutation conferring resistance to ketolides is shown by an arrow (SEQ ID NO:2).

In FIG. 1, the DNA oligonucleotide primer contains a fluorescent dye modification (shown by ###) and the extension reaction will be performed in the presence of dAPT, dTTP, dGTP and ddCTP. The main DNA products on the gel after primer extension correspond to the primer itself, the extension product resulting from reverse transcriptase pausing at the DMS modified position A752 (bold), the extension product resulting from reverse transcriptase pausing at the DMS-modified position A753, and extension product resulting from termination of the transcription due to incorporation of ddC. The ratio of the longest band (termination at G748) and the third longest band (pausing at DMS-modified A752) will reflect the extent of A752 protection by bound antibiotics.

The examples herein relate to a footprinting assay in the domain II of 23S RNA of *E. coli* having strong interaction in the vicinity of position 752–754 with antibiotics. In the examples, the ketolides which are active against erythromycin resistant strains were studied and similarities and differences in ketolide and macrolide interaction within 2 distinct domains of 23S ribosomal RNA were found.

Ketolides are derivatives of erythromycin without cladinose in position 3 and these compounds have antibiotic properties [Antimicrobial Agents and Chemotherapy 1997, Vol. 41 p. 2149 to 2158 or 1997, Vol. 41, p. 454 to 459 or Lettres de l'infectiologue 1997, Vol. 12 p. 46 to 54].

Ketolides are described, for example, in European patents No. 0,487,411, No. 596,802, No. 606,024, No. 614,905, No. 680,967 and in French patent application No. 2,742,757. Hereafter, we use more specifically products A and B.

11,12-dideoxy-3-de((2,6-dideoxy-3-C-methyl-3-O-methyl-alpha-L-ribohexopyranosyl)oxy)-6-O-methyl-3-oxo-12, 11-(oxy-carbonyl(2-(3-(4-quinoleinyl)propyl) hydrazono))-erythromycin called hereafter product A.

11,12-dideoxy-3-de((2,6-dideoxy-3-C-methyl-3-O-methyl-alpha-L-ribohexopyranosyl)oxy)-6-O-methyl-3-oxo-12, 11-(oxy-carbonyl(4-(4-(3-pyridinyl)-1H-imidazol-1-yl) butyl)imino))-erythromycin called hereafter product B.

The results of the examples may be summarized in the following way. Ketolides protect A2058 and A2059 in the domain V of 23S rRNA and A752 in domain II. In contrast, erythromycin, which also protects A2058 and A2059, enhanced modification of A752. This indicates a difference in the mode of interaction of erythromycin and ketolides with domain II.

Ketolide-resistance mutation was found in domain II of 23S rRNA close to the position protected by ketolide, confirming a strong interaction of the antibiotic with this rRNA site. Footprinting experiments in the domain II of 23S rRNA of E. coli demonstrated strong interactions in the vicinity of positions 752–754 with antibiotics. Therefore, footprinting in domain II, which can be automated and performed on a large scale format, may be an easy, fast and inexpensive way to screen drug derivatives. Mutations in these positions confer resistance to ketolide whereby these mutants obtained could be used for a screening to find new antibiotics.

Ketolides are ribosome-targeted antibacterial antibiotics which bind to a large subunit and inhibit translation. The mode of interaction of ketolides with the ribosome is different from that of erythromycin, roxithromycin and other macrolides.

Chemical RNA footprinting was used to get a better understanding of the difference between interaction of product A and other macrolides with the ribosome. No significant difference between interaction with the domain V, the known site of erythromycin binding, was observed as both erythromycin and product A or B protected the same two positions, A 2058 and A 2059, of 23S rRNA from modification with dimethyl sulfate. However, while ketolides also strongly protected A752 in domain II, binding of erythromycin to the ribosome increased accessibility of A752 to chemical modification suggesting that ketolides and erythromycin form different contacts with rRNA in the vicinity of A752.

A strong interaction of ketolides with domain II became evident when a dominant mutation (U754A) in E. coli 23S rRNA was found to render cells resistant to ketolides. The proximity of the isolated mutation to the site of the ketolide footprint confirms an importance of interaction of the drug with domain II. A strong interaction in domain II may account for a high activity of products A and B and other ketolides towards erythromycin-resistant ribosomes (e.g. S. pneumoniae) containing modifications of nucleotides in domain V. At the same time, the current results are also compatible with a model for two binding sites of ketolides on the ribosome, one involving domain V and another involving domain II.

In the following examples, there are described several preferred embodiments to illustrate the invention. However, it is to be understood that the invention is not intended to be limited to the specific embodiments.

EXAMPLE

Materials

E. coli 70S ribosomes were isolated from MRE 600 strain according to the method described by Spedding [Isolation and analysis of ribosomes from prokaryotes, eukaryotes, and organelles. Ribosomes and Protein Synthesis, A Practical Approach, 1990 pp. 1–29, Oxford University Press, Oxford.]

Erythromycin, Product A and Product B were used in freshly dissolved solutions in ethanol at a 5 mM concentration and the dimethyl sulfate (DMS) was from Aldrich.

Method

Ribosomes were heat-activated by incubation for 5 minutes at 42° C. and 10 pmol of 70 S ribosomes were incubated for 10 minutes at 37° C. and then for 10 minutes at 20° C. in 50 $\mu$l of a buffer (80 mM potassium cacodylate, pH 7.2, 20 mM, $MgCl_2$, 100 mM $NH_4Cl$) in the absence or in the presence of 5 $\mu$M or 50 $\mu$M of erythromycin or Product A or Product B. Modification of rRNA was effected by the method of Stern et al. [Analysis of RNA structure using chemical and enzymatic probing monitored by primer extension. Methods Enzymol., Vol. 164, pp. 481–489, (1988)].

2 $\mu$l of DMS were added and the samples were incubated for 10 minutes at 37° C. and then placed in ice. Then, 50 $\mu$l of a DMS-stop buffer [300 mM sodium acetate, pH 5.5, 100 mM mercaptoethanol] were added to the samples followed by the addition of 300 $\mu$l of cold ethanol. Ribosomes were pelleted by centrifugation for 10 minutes at 14,000 g and the ribosome pellets were resuspended in 200 $\mu$l of a buffer (300 mM sodium acetate, pH 5.5, 5 mM EDTA, 0.5% SDS). The suspensions were extracted twice with water saturated phenol, once with a 1:1 (v/v) chloroform-phenol mixture and once with chloroform. RNA was precipitated by addition of 3 volumes of ethanol and centrifugation for 10 minutes at 14,000 g.

The resulting pellets were dissolved in 50 $\mu$l of water and reverse-transcriptase-mediated primer extension was effected according to Stern et al (see above). The rRNA was annealed to the primer by mixing 2.5 $\mu$l of the RNA solution above with 1 $\mu$l of [$^{32}P$] radiolabelled deoxyoligo ribonucleotide primer (SEQ ID NO:3) (GGAGAACCAGCTATCTC) or radiolabeled deoxyoligo ribonucleotide primer (SEQ ID NO:4) (CAAAGCCTCCCACCTATCCT) complementary to the 23S rRNA sequence 800–815 or 2114–2135, respectively, and 1 $\mu$l of 4.5×hybridization buffer (225 mM K-Hepes, pH 7.0, 450 mM KCl). The samples were incubated for 30 seconds at 90° C. and cooled to about 50° C. over a 15 minute period.

3 $\mu$l of an extension mixture containing 0.67 $\mu$l of buffer (1.3 M Tris-HCl, pH 8.5, 100 mM DTT), 1.5 $\mu$l of 1 mM dNTP mix (1 mM each dNTP), 0.73 $\mu$l of $H_2O$ and 0.1 $\mu$l reverse transcriptase (Seikagaku America, Inc.) were added to the rRNA/primer mixture and the mixture was incubated at 42° C. for 20 minutes. Then, 1 $\mu$l of 1 mM dNTP mix was added and incubation was continued for 20 minutes at 42° C. The reaction was stopped by addition of 120 $\mu$l of a stop buffer (1 vol 0.3 M NaAc, pH 5.5, 3 vol of ethanol) and nucleic acids were precipitated by centrifugation for 10 minutes at 14,000 g. The pellets were dissolved in several $\mu$l of a gel-loading buffer containing trace dyes dissolved in 95% formamide. The samples were heated for 3 minutes at 100° C. and then loaded onto 6% sequencing gel. After the run, gel was exposed to X-ray film or was scanned on a phosporo imager to quantify the radioactive bands.

Footprinting provides a snapshot of rRNA sites that may be involved with interaction with an antibiotic. Previously, Moazed et al [Biochemie, Vol. 69 (1987) p. 879–884] showed that erythromycin protected several positions in the central loop of domain V (A2058, A2059 and G 2505). Comparison of the footprints of erythromycin and Product A above in domain V showed the same very strong protection of A2058 and A2059. Since only DMS was used in the footprinting, G2505 could not be seen.

It can be concluded that interaction of erythromycin and ketolides in domain V are very similar, at least from the RNA footprinting results. Both erythromycin and Products A and B affected modification of another position in 23S, rRNA, A752. However, the effects of erythromycin and Products A and B were drastically different in this case. Products A and B protected A752 from chemical modification in 70S ribosome, but erythromycin made this position more accessible to chemical modification. Moazed et al. noticed that vernamycin B, a group B component of streptogramin antibiotics, protected A752, but the effects of erythromycin at this position were not reported (Biochemie, Vol. 69 (1987) pp 879–884).

The above results show that erythromycin, ketolides and streptogramin group B antibiotics all interact not only with domain V but also with domain II (position 752). The footprinting results also show the interaction of ketolides and erythromycin in domain II is different resulting in protection of A752 in the case of ketolides and enhancement of modification in the case of erythromycin. A strong protection afforded by ketolide in domain II may indicate a more tight interaction of the drug with this site in rRNA which might explain in part a stronger effect of ketolides on bacteria with MLS type resistance. Strong binding in domain II may still be sufficient to overcome a negative effect of A2058 methylation on the antibiotic binding.

If this model is correct, it can be predicted that antibiotics showing strong protection in domain II should generally be more potent in overcoming MLS resistance. Therefore, footprinting in domain II which can be automated and performed on a large scale can be an easy, fast and inexpensive method to screen antibiotic derivatives.

The RNA footprinting method provides essential information about rRNA bases located in the vicinity of an antibiotic, but one of the drawbacks of the method is that the antibiotic binding is performed in vitro. This means that all the limitations of the artificial in vitro system affect the footprinting results. Therefore, rRNA mutations rendering live cells ketolide resistant were used in the next step with pKK3535 plasmid containing a complete rRNA operon of E. coli. Plasmid pKK3535 was described by Brosius et al. [Gene organization and primary structure of a ribosomal RNA operon from Escherichia coli. Journal of Molecular Biology vol. 148 (1981) pp. 107–127].

When the said plasmid was introduced into the bacterial cell, 50 to 60% of the ribosomes contain plasmid-encoded RNA. If the plasmid-borne rRNA operon contains an antibiotic-resistant mutation, then at least half of the ribosomes will become tolerant to the antibiotic and the cell may exhibit resistance phenotype. To select ketolide-resistant mutations in rRNA, pKK3535 plasmid was randomly mutagenized by introducing it into a mutator strain and growing the cells for several generations which resulted in an accumulation of random point mutations scattered all over the plasmid.

The randomly mutagenized plasmid was then isolated from the mutator strain and introduced into an E. coli JM109 strain. Transformed cells were plated onto agar plates containing 100 µg/ml of ampicillin per 60 µg/ml of Product B and resistant colonies were selected.

To map the mutation, the 23S rRNA gene on the isolated pKK3535 plasmid was sequenced and a mutation in domain II of the 23S rRNA was found, where U754 was substituted by A. The proximity of the identified mutation (U754) to the position protected by ketolides (A752) clearly confirmed the previous conclusion that ketolides interact with the ribosomal RNA in domain II, in the vicinity of positions 752–754. Mutation of U754A disrupted a Watson-Crick basepair close to the loop of the helix. Most probably, this mutation should affect conformation of the helix loop, where the antibiotic-binding site can be located.

To demonstrate that mutation U754A is sufficient to confer resistance to Product B, the fragment of the 23S rRNA gene, which was completely sequenced to verify the absence of the mutations other than U754A, was used to replace a homologous wild type fragment in the pKK3535 plasmid. Introduction of the resulting plasmids into E. coli JM 109 cells rendered them resistant to Product B, clearly proving a correlation between the presence of the U754A mutation in the 23S rRNA gene and the resistance to Product B.

Various modifications of the method of the invention may be made without departing from the spirit or scope thereof and it is to be understood that the invention is intended to be limited only as in the appended claims.

What I claim is:

1. A method of screening for antibiotic induced protection against erythromycin resistant strains, comprising footprinting an antibiotic on domain II of 23S rRNA by incubating an antibiotic with ribosomes, modifying ribosomes with a chemical modifying agent, isolating modified rRNA, subjecting it to reverse transcriptase-mediated primer extension and gel electrophoresis on a DNA sequencer and determining the ratio of the bands of sequencer to ascertain the extent of antibiotic-induced protection of an rRNA nucleotide from chemical modification.

2. The method of claim 1 wherein the ribosomes are from *Escherichia coli*.

3. The method of claim 1 wherein the ribosomes are from any organism other than *Escherichia coli*.

4. The method of claim 1 wherein the footprinting is performed in a multiwell plate.

5. The method of claim 3 wherein the multiwell plate is a 96 well plate.

6. The method of claim 1 wherein a fluorescent dye labelled primer is used for the primer extension.

7. The method of claim 1 wherein the gel electrophoresis is performed on a DNA sequencer with multiple loadings of the samples into the same wells.

8. The method of claim 1 wherein the steps are automated.

* * * * *

SEQUENCE LISTING (1) GENERAL INFORMATION:

(iii) NUMBER OF SEQUENCES:  4

(2) INFORMATION FOR SEQ ID NO: 1:

(i) SEQUENCE CHARACTERISTICS:
      (A) LENGTH:  40 BASE PAIRS
      (B) TYPE:  NUCLEIC ACID
      (C) STRANDEDNESS:  SINGLE
      (D) TOPOLOGY:  UNKNOWN (ii) MOLECULE TYPE:  rRNA (xi) SEQUENCE DESCRIPTION:  SEQ  ID NO:1:

CCGACUAAUG UUGAAAAAUU AGCGGAUGAC UUGUGGCUGG          40

(2) INFORMATION FOR SEQ ID NO: 2:

(i) SEQUENCE CHARACTERISTICS:
      (A) LENGTH:  29 BASE PAIRS
      (B) TYPE:  NUCLEIC ACID
      (C) STRANDEDNESS:  SINGLE
      (D) TOPOLOGY:  UNKNOWN (ii) MOLECULE TYPE:  rRNA (xi) SEQUENCE DESCRIPTION:  SEQ  ID NO:  2:

-continued

```
AACCGACUAA UGUUGAAAAA UUAGCGGAU                                29

(2) INFORMATION FOR SEQ ID NO:3:

(i) SEQUENCE CHARACTERISTICS:
        (A) LENGTH:  17 BASE PAIRS
        (B) TYPE:  NUCLEIC ACID
        (C) STRANDEDNESS:  SINGLE
        (D) TOPOLOGY:  UNKNOWN (xi) SEQUENCE DESCRIPTION:  SEQ  ID NO:3:

GGAGAACCAG CTATCTC                                             17

(2) INFORMATION FOR SEQ ID NO:4:

(i) SEQUENCE CHARACTERISTICS:
        (A) LENGTH:  20 BASE PAIRS
        (B) TYPE:  NUCLEIC ACID
        (C) STRANDEDNESS:  SINGLE
        (D) TOPOLOGY:  UNKNOWN (xi) SEQUENCE DESCRIPTION:  SEQ  ID NO:4:

CAAAGCCTCC CACCTATCCT                                          20
```